United States Patent [19]

Nilsson et al.

[11] Patent Number: 4,935,365

[45] Date of Patent: Jun. 19, 1990

[54] MACROPOROUS PARTICLES FOR CELL CULTIVATION OR CHROMATOGRAPHY

[76] Inventors: Kjell G. C. Nilsson, Traktorgranden 4, S-222 51 Lund, Sweden, S-222 51; Klaus H. Mosbach, Lackalanga 31-38, S-244 02 Furulund, Sweden, S-244 02

[21] Appl. No.: 919,325

[22] Filed: Oct. 15, 1986

[30] Foreign Application Priority Data

Oct. 15, 1985 [SE] Sweden ................................ 8504764

[51] Int. Cl.$^5$ ...................... C12N 11/10; C12N 11/02; C12N 5/02; B01N 13/02
[52] U.S. Cl. .................................... 435/178; 435/177; 435/180; 435/182; 435/240.24; 264/4.1; 264/4.6; 264/4.7; 530/354
[58] Field of Search ............... 435/174, 175, 177, 180, 435/182, 240.24; 530/354; 106/122; 521/102; 264/4.1, 4.6, 4.7, 49, 50

[56] References Cited

U.S. PATENT DOCUMENTS

| | | | |
|---|---|---|---|
| 2,712,672 | 7/1955 | Calcagno | 264/49 X |
| 3,627,708 | 12/1971 | Morse et al. | 260/2.5 B |
| 3,838,007 | 9/1974 | Van Velzen | 435/177 X |
| 3,841,971 | 10/1974 | Messing | 435/175 |
| 4,025,391 | 5/1977 | Kawashima et al. | 435/180 |
| 4,085,203 | 4/1978 | Telling et al. | 435/240.24 |
| 4,144,126 | 3/1979 | Burbidge | 435/240.24 X |
| 4,157,424 | 6/1979 | Boutle | 264/49 X |
| 4,163,691 | 8/1979 | Devos et al. | 435/174 |
| 4,373,027 | 2/1983 | Berneman et al. | 435/240.24 |
| 4,411,999 | 10/1983 | Shigesada et al. | 435/174 X |
| 4,416,813 | 11/1983 | Ikeda et al. | 435/177 X |
| 4,500,358 | 2/1985 | Mayer et al. | 106/122 |
| 4,530,905 | 7/1985 | Freedman | 435/177 |
| 4,609,403 | 9/1986 | Wittmer et al. | 106/122 |
| 4,647,536 | 3/1987 | Mosbach et al. | 435/177 |
| 4,798,786 | 1/1989 | Tice et al. | 435/177 |

FOREIGN PATENT DOCUMENTS

| | | |
|---|---|---|
| 0168622 | 4/1981 | European Pat. Off. . |
| 0047064 | 11/1981 | European Pat. Off. . |
| 0025639 | 3/1982 | European Pat. Off. . |
| 82/00660 | 3/1982 | PCT Int'l Appl. ............ 435/240.24 |
| 86/05811 | 10/1986 | PCT Int'l Appl. . |

*Primary Examiner*—David M. Naff
*Attorney, Agent, or Firm*—Poms, Smith, Lande & Rose

[57] ABSTRACT

Particles which enclose cavities can be produced by adding a water-insoluble solid, liquid or gaseous cavity generating compound to an aqueous solution of a matrix material. Subsequent to forming particles by dispersion in a water-insoluble dispersion medium, the matrix is rendered insoluble in water by cooling, by covalent cross-linking or by polymerization. The cavity generating compound is washed out, whereafter the particles can be used as ion exchangers in gel filtration processes, in hydrophobic chromatography or in affinity chromatography, optionally subsequent to derivatizing the particles. The particles can also be used to advantage as microcarriers in the cultivation of anchorage dependent cells.

10 Claims, No Drawings

MACROPOROUS PARTICLES FOR CELL CULTIVATION OR CHROMATOGRAPHY

The separation of molecules is effected to a large extent with the aid of matrices which have connected thereto ligands which interact with the molecules concerned. These ligands may be ionic, hydrophobic or affinity ligands. Electrically neutral matrices of mutually different porosity are used when separating molecules in accordance with size, gel filtration. These matrices are normally spheroidal in shape, in order to afford good flow properties. The flow properties of the separation system are also determined by the size of the particles present; the smaller the particle the higher the pressure drop, which results in a lower rate of flow. It is desirable in industrial applications to achieve high rates of flow, so that the molecules can be separated quickly. Another important parameter with regard to the particles used is the total specific surface area presented by the particles. The larger the specific surfaces area the more quickly the molecules are able to penetrate the matrix and interact with the ligands. This specific surface area can be increased by reducing the sizes of the particles.

This antithesis is usually solved by taking a middle path, i.e. by using a relatively large particle size which is not optimum with regard to either the flow properties of the separation system or the specific surface area.

We, the inventors, have overcome the antithesis by manufacturing particles which enclose a large number of cavities, so that the particles can be given a size which while enabling a high rate of flow to be achieved also present a very large specific surface area. In addition to the separation of molecules, the extremely large surface area of the particles provided enables the particles to be used for cultivating anchorage dependent cells. In this technique, the anchorage dependent cells are allowed to grow on the surfaces of particles, microcarriers, suspended in a nutrient. Because the interiors of the particles can now also be used in cell cultivation processes, the surface area available is much larger and mechanical protection is also afforded to the cells during the process of cultivation.

These macroporous particles are produced by admixing a cavity generating compound with an aqueous solution of the matrix forming compound. The cavity generating compound may be solid, liquid or gaseous. The resultant mixture is then dispersed in a water-insoluble dispersion medium, to form particles therein. The matrix is then made insoluble in water by cooling the system, by covalent cross-linking or by polymerization. Subsequent to the removal of the cavity generating compound, the resultant macroporous particles can either be derivatized or used directly for their intended purposes.

The matrix forming compound is selected from proteins, polysaccharides or synthetic polymers. Examples of compounds which can be used are:
proteins—gelatin, albumin
polysaccharides—dextran, agarose
synthetic polymers—polyacrylamide.

An example of a solid cavity generating compound is calcium carbonate, which after the particles have been produced by dispersing the mixture in a water-insoluble dispersion medium and the matrix has been made insoluble in water, can be removed by treating the system with an acid.

When the cavity generating compound used is in liquid form, it is necessary to add an emulsifier. The liquid water-insoluble cavity generating compound is admixed with a water-insoluble emulsifier (characterized by an HLB-value greater than 89). Droplets of cavity generating compound are formed by adding said compound containing a water-insoluble emulsifier (characterized by an HLB-value lower than 8) to the aqueous solution of the matrix continuously while stirring the system; the more vigorous the agitation the smaller the droplets formed. When the cavity generating compound has been added in an amount sufficient to saturate the aqueous solution of matrix material, further addition will cause the matrix solution to form an excess of droplets of the cavity generating compound. The excess droplets of cavity generating compound forms a water-insoluble dispersion medium in which droplets of the matrix material are dispersed. The droplets of matrix material dispersed in the excess cavity generating material are saturated with internal droplets of the previously added cavity generating compound. By selecting emulsifiers which result in stable dispersions, particles of matrix material which contain droplets of the cavity generating compound are obtained, subsequent to rendering the matrix material insoluble in water. The cavity generating compound is then washed out with a solvent. The majority of organic solvents (water insoluble) can be used as the liquid cavity generating compound, as can also vegetable oils or mineral oils. Examples of suitable emulsifiers are Span 85, Arlacel 83 (water insoluble) and Tween 80, Triton X-100 (water soluble).

When the cavity generating compound used is in gas form, the gas is blown under high pressure through an aqueous solution of the matrix, which contains a water-soluble emulsifier, in order to generate stable gas bubbles in the system. The mixture is then dispersed in a water-insoluble dispersion medium, to obtain particles. A water-insoluble emulsifying agent is also added to the dispersion medium, in order to obtain a stable dispersion. The emulsifiers and dispersion medium are removed subsequent to rendering the particles insoluble in water.

EXAMPLE 1

Thermal gelation (liquid cavity generating compound)

Gelatin was dissolved by heating the same in water to a concentration of 10% (w/v). 6 g of emulsifier (Tween 80) were added to 100 ml of the gelating solution. 500 ml of toluene containing 30 g emulsifier (Span 85) were then stirred into the solution. The initial amount of toluene added acts as a cavity generating compound which is dispersed as droplets within the gelatin solution. As more toluene is added, the gelatin solution becomes saturated with toluene droplets and eventually sufficient toluene is added (i.e., 500 ml) so that the gelatin solution be-comes aqueous gelatin droplets dispersed in a toluene solution. When beads of the desired size had formed, the dispersion was cooled to a temperature beneath the solidification temperature of the gelatin. The aforedescribed process results in the formation of gelatin beads which are saturated with droplets of toluene. These toluene droplets can be removed by washing the beads with ethanol and acetone, therewith providing a gelatin bead which is filled with cavities.

The gelatin beads can then be cross-linked with, for example, glutardialdehyde, in order to further increase stability.

EXAMPLE 2

Thermal gelation (gaseous cavity generating compound)

5 g of emulsifier (Triton x-100) were added to 100 ml of gelatin solution (10% w/v). Air under high pressure was then blown through the solution, to form a large number of air bubbles therein. Beads were formed by dispersing the solution in 500 ml toluene/chloroform (73/27, w/v) containing 30 g emulsifier (Span 85), while stirring the system. Subsequent to obtaining beads of the desired size, the dispersion was cooled, so as to solidify the gelatin. The organic solvents were then removed, by washing with ethanol and acetone. The gaseous cavity generating compound escapes automatically from the resultant beads due to their high porosity. The resultant beads can then be cross-linked further with, for example, glutardialdehyde.

EXAMPLE 3

Thermal gelation (solid cavity generating compound)

10 g of calcium carbonate were added to 100 ml of gelatin solution (10% w/v), whereafter beads were produced in accordance with Example 2. The beads were treated with acid, so as to dissolve the calcium carbonate and therewith form cavities in the beads.

EXAMPLE 4

Polymerization

Acrylamid (17 g) and bisacrylamide (1.2 g) were dissolved in a Tris-buffer (100 ml, 0.05M, pH 7). Ammonium persulphate (0.5 g/ml, 0.25 ml) and emulsifier (Triton x-100, 6 g) were added to the monomer solution. 500 ml of toluene containing an emulsifier (Span 85, 30 g) were then stirred into the system. TEMED (co-catalyst, 1.3 ml) was then added to the system. The organic solvents were washed out with ethanol and acetone, upon termination of the polymerization process.

EXAMPLE 5

Covalent cross-linking

Sodium hydroxide (0.7 g) and emulsifier (Tween 80, 6 g) were added to an aqueous solution of dextran (10%, w/v, 100 ml). Toluene (500 ml) having an emulsifier (Span 85, 30 g) and epichlorohydrin (1.5 g) dissolved therein was then added to the solution while stirring the system. The temperature of the system was raised to 40° C. over a period of 2 hours, and then to 70° C. over a further period of 12 hours. The resultant beads were washed with ethanol and acetone, in order to remove organic solvent The properties of the beads formed can be varied, by varying the quantity of dextran and the quantity of epichlorohydrin used.

EXAMPLE 6

Covalent cross-linking

Chitosan was dissolved in formic acid (5%, w/v) to a concentration of 30 g/l. 100 ml of solution were admixed with emulsifier (Tween 80, 6 g) and, while stirring the system, with toluene (500 ml) containing an emulsifier (Span 85, 30 g). Subsequent to obtaining beads of the desired size, formaldehyde (20 ml) was added to the system. The resultant beads were washed with methanol after a time lapse of one hour.

We claim:

1. Macroporous particles for use as a cell cultivation matrix material or as a chromatography matrix material, said macroporous particles having a particle size of about 10–500 micrometers and including a large number of pores having a diameter of about 1–50 micrometers wherein said particles are formed by the steps of:

dissolving a water-soluble matrix material in an aqueous solvent to form an aqueous solution comprising said matrix material dissolved in said aqueous solvent;

mixing a sufficient amount of a water-insoluble liquid cavity generating compound with said aqueous solution of matrix material to form a dispersion of droplets of said liquid cavity generating compound in said aqueous solution;

adding additional liquid cavity generating compound to said dispersion in an amount sufficient to saturate said dispersion and form droplets of said dispersion dispersed in said liquid cavity generating compound;

solidifying said dispersed droplets to form beads of said matrix material having a large number of pores containing said liquid cavity generating compound dispersed therethrough;

separating said solidified beads from said liquid cavity generating compound; and removing said liquid cavity generating compound from the pores of said beads to form said macroporous particles having a particle size of between about 10 to 500 micrometers and a large number of pores having diameters of between about 1-50 micrometers.

2. Macroporous particles according to claim 1 wherein said dispersed droplets in the liquid cavity generating compound are solidified by cooling.

3. Macroporous particles according to claim 1 wherein said dispersed droplets in the liquid cavity generating compound are solidified by polymerization.

4. Macroporous particles according to claim 1 wherein said aqueous solution of matrix material includes an emulsifier to promote dispersion of said cavity generating compound when forming said dispersion of the cavity generating compound.

5. Macroporous particles according to claim 1 wherein said liquid cavity generating compound includes an emulsifier to promote dispersion of said droplets of the dispersion of the cavity generating compound within said cavity generating compound prior to said solidification of said droplets.

6. Macroporous particles according to claim 1 wherein said pores have a diameter of between about 10-20 micrometers.

7. Macroporous particles according to claim 1 wherein said water-soluble matrix material is a protein, polysaccharide or synthetic polymer.

8. Macroporous particles according to claim 7 wherein said water-soluble matrix material is gelatin.

9. Macroporous particles according to claim 1 wherein said cavity generating compound is toluene.

10. Macroporous particles according to claim 1 containing attached anchorage dependent cells.

* * * * *